United States Patent [19]

Sallee et al.

[11] Patent Number: 5,721,273
[45] Date of Patent: Feb. 24, 1998

[54] USE OF CERTAIN 9-HALO-13,14-DIHYDROPROSTAGLANDINS TO TREAT GLAUCOMA AND OCULAR HYPERTENSION

[75] Inventors: Verney L. Sallee, Burleson; Louis DeSantis, Jr.; Paul W. Zinke, both of Fort Worth; John E. Bishop, Arlington, all of Tex.

[73] Assignee: Alcon Laboratories, Inc., Fort Worth, Tex.

[21] Appl. No.: 167,470

[22] Filed: Dec. 15, 1993

[51] Int. Cl.$^6$ .................... A61K 31/215; A61K 31/19
[52] U.S. Cl. .................... 514/530; 514/573; 514/913
[58] Field of Search .................... 514/530, 573, 514/913

[56] References Cited

U.S. PATENT DOCUMENTS

| | | |
|---|---|---|
| 4,444,788 | 4/1984 | Skuballa et al. |
| 4,454,339 | 6/1984 | Skuballa et al. |
| 4,789,685 | 12/1988 | Skuballa et al. |
| 5,004,752 | 4/1991 | Raduechel et al. |
| 5,079,259 | 1/1992 | Skuballa et al. |
| 5,093,329 | 3/1992 | Woodward. |
| 5,204,371 | 4/1993 | Skuballa et al. |

FOREIGN PATENT DOCUMENTS

| | | |
|---|---|---|
| 0 253 094 A2 | 1/1988 | European Pat. Off. |
| 299 914 B1 | 7/1988 | European Pat. Off. |
| 0 561 073 A1 | 9/1993 | European Pat. Off. |
| 42 29 048 A1 | 3/1994 | Germany. |
| 42 29 050 A1 | 3/1994 | Germany. |
| 42 29 051 A1 | 3/1994 | Germany. |
| WO 90/02553 | 3/1990 | WIPO. |

OTHER PUBLICATIONS

Braun, et al., "Effect of ZK 110.841 on Cerebral Vascular Contraction and TXA$_2$-Release Caused by Thrombin-Stimulated Platets," *Archives of Pharmacology*, 339 Suppl:R37(148) (1989).

Ney, "Potent Inhibition of FMLP-Induced Neutrophil Activation by the PGD$_2$ Analogue ZK 110.841," *Archives of Pharmacology*, 339 Suppl:R38 (150) (1989).

"New Research Drug DLO/8149" Drug License Opportunities (IMSWORLD Publications) (Jun. 25, 1990).

Buchmann et al., "Synthesis of a Chemical and Metabolically Stable and Biologically Potent PGD$_2$-Analogue," *Tetrahedron Letters*, 31(24):3425–3428 (1990).

Nakajima et al., *Graefe's Arch. Clin. Exp. Ophthalmol.*, 229:411–413 (1991).

Woodward et al., *Invest. Ophthalmol. Vis. Sci.*, 31:138–146 (1990).

Thierauch et al., *Prostaglandins*, 35:6:855–868 (1988).

Goh et al., *Graefe's Arch. Clin. Exp. Ophthalmol.*, 227:476–481 (1989).

Thierauch, et al., *Advances in Prostaglandin, Thromboxane and Leukotriene Research*, 19:655–658 (1989).

Woodward et al., *Invest. Ophthal. & Vis. Sci.*, 31:1:138–146 (1990).

Chemical Abstracts 113:211633, 1990. Buchmann et al.

*Primary Examiner*—Zohreh Fay
*Attorney, Agent, or Firm*—Barry L. Copeland

[57] ABSTRACT

9-Halo-13,14-dihydroprostaglandins are useful in the treatment of glaucoma and ocular hypertension. Also disclosed are ophthalmic, pharmaceutical compositions comprising such prostaglandins.

9 Claims, 1 Drawing Sheet

USE OF CERTAIN 9-HALO-13,14-DIHYDROPROSTAGLANDINS TO TREAT GLAUCOMA AND OCULAR HYPERTENSION

BACKGROUND OF THE INVENTION

The present invention relates to the use of prostaglandins and prostaglandin analogues for the treatment of glaucoma and ocular hypertension. As used herein, the terms "prostaglandin" and "PG" shall refer to prostaglandins and derivatives and analogues thereof, except as otherwise indicated by context.

Naturally-occurring prostaglandins, including prostaglandins of the F series (such as $PGF_{2\alpha}$), the E series (such as $PGE_2$) and the D series (such as $PGD_2$), are known to lower intraocular pressure (IOP) after topical ocular instillation, but can cause marked conjunctival hyperemia and/or inflammation with a number of associated side effects. There have been many attempts to synthesize prostaglandin derivatives which are more effective at lowering IOP and/or which have reduced side effects. Such attempts have been made by Stjernschantz et al. (WO 90/02553) and Woodward (U.S. Pat. No. 5,093,329) to selectively reduce or eliminate the side effects while maintaining the IOP-lowering effect.

SUMMARY OF THE INVENTION

It has now been unexpectedly discovered that certain 9-halo-13,14-dihydroprostaglandins are significantly more effective in lowering IOP than other, known prostaglandins. In particular, the compounds of the present invention have unexpectedly been found to lower IOP between about 40 to 50%, with greatly reduced side effects, particularly with respect to hyperemia.

DETAILED DESCRIPTION OF THE INVENTION

Figure 1:
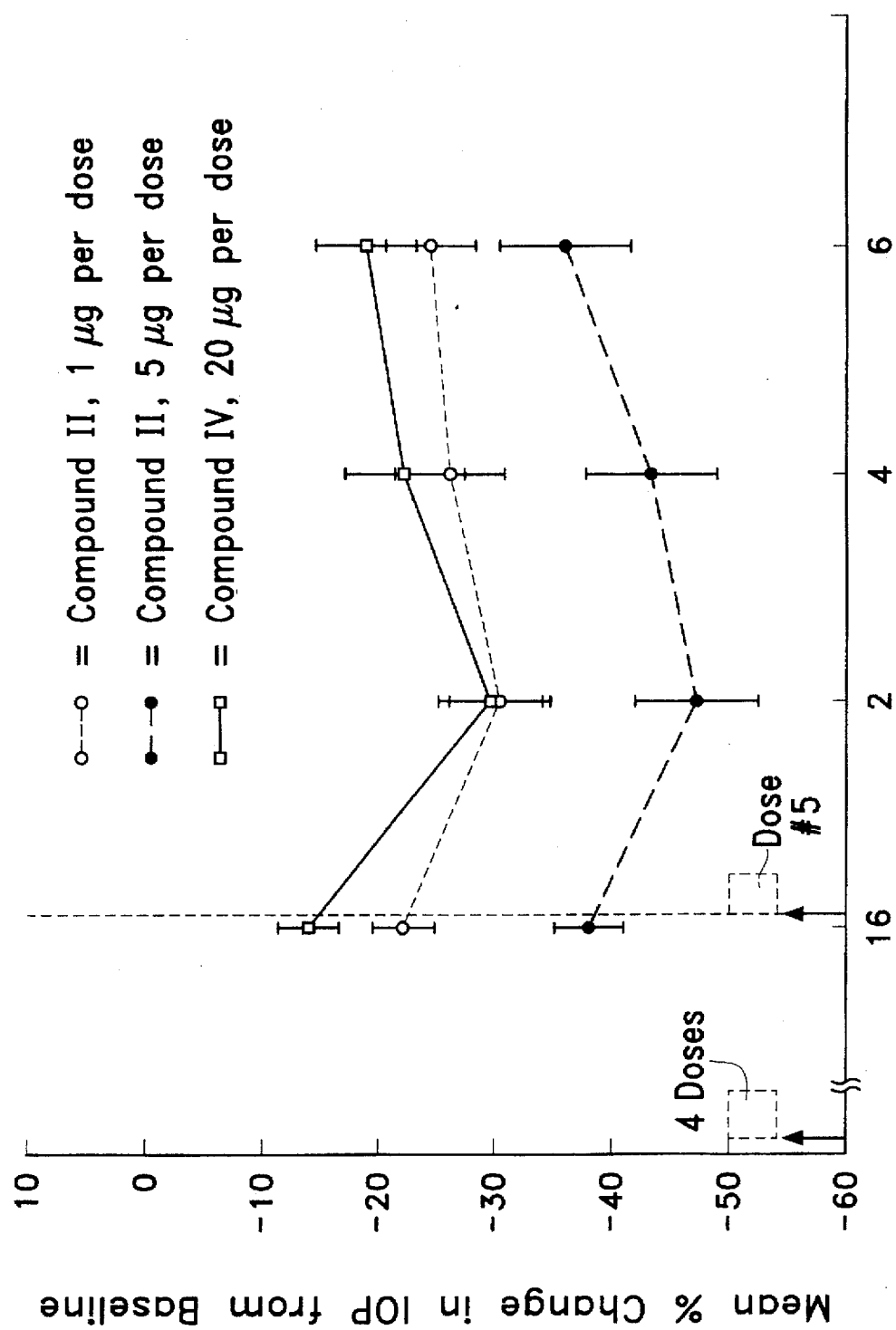
FIG. 1 graphically illustrates the results of the study presented in Example 4.

The 9-halo-13,14-dihydroprostaglandins which are useful in the compositions of the present invention have the general formula:

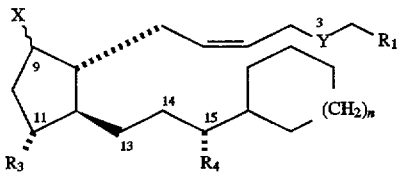

wherein $R_1=CO_2R_2$, wherein $R_2=H$, a cationic salt moiety, or an ophthalmically acceptable ammonium moiety; or $R_1$ may also represent an ophthalmically acceptable ester moiety;

X=halogen, particularly Cl or F, in either configuration;

Y=$CH_2$ or O;

$R_3$, $R_4$ can be the same or different, and are selected from: free or functionally modified hydroxy groups; and n=0 or 1.

As used in this specification, the term "ophthalmically acceptable ester moiety" refers to an ophthalmically acceptable ester moiety which hydrolyzes to the parent acid upon topical delivery to the eye. Examples of ophthalmically acceptable esters include, but are not limited to: $R_2$=substituted or unsubstituted alkyl, cycloalkyl, (cycloalkyl)alkyl, aryl, arylalkyl, heteroaryl, or (heteroaryl)alkyl, wherein substituents include alkyl, halo, a free or functionally modified hydroxy group, or a free or functionally modified thiol. As used in this specification, the term "heteroaryl" refers to a monocyclic ring system of 5 or 6 atoms composed of C, N, O, and/or S, such as furan, thiophene, pyrrole, pyrazole, imidazole, triazole, tetrazole, oxazole, isothiazole, thiazole, thiadiazole, pyridine, pyrimidine, pyradazine and pyrazine. Similarly, $R_3$ and $R_4$ represent either free hydroxy groups or acylated (esterified) hydroxy groups which hydrolyze to the parent hydroxy groups upon topical delivery to the eye.

It is preferred to use compounds of formula (I) wherein: $R_1=CO_2R_2$; $R_2=H$, methyl, ethyl, n-propyl, isopropyl, t-butyl or benzyl; X=Cl in the β (R) configuration; Y=O or $CH_2$; $R_3$ and $R_4$=OH; and n=1. It is most preferred to use compounds of formula (I) wherein: $R_1=CO_2R_2$; $R_2=H$, methyl, ethyl, isopropyl or t-butyl; X=Cl in the β (R) configuration; Y=O; $R_3$ and $R_4$=OH; and n=1.

Preferred compounds include:

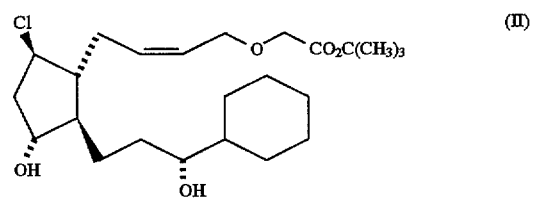

(5Z)-(9R, 11R, 15R)-9-Chloro-15-cyclohexyl-11,15-dihydroxy-3-oxa-16,17,18,19,20-pentanor-5-prostenoic Acid t-Butyl Ester

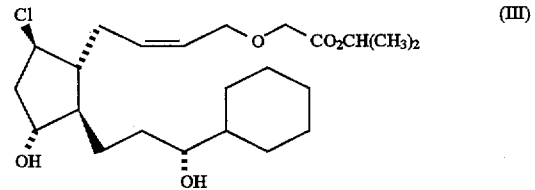

(5Z)-(9R, 11R, 15R)-9-Chloro-15-cyclohexyl-11,15-dihydroxy-3-oxa-16,17,18,19,20-pentanor-5-prostenoic Acid Isopropyl Ester

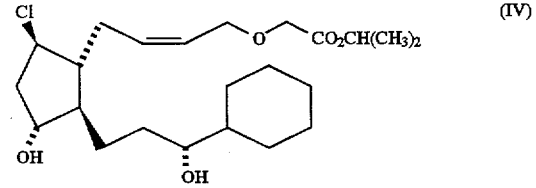

(5Z)-(9R, 11R, 15R)-9-Chloro-15-cyclohexyl-11,15-dihydroxy-16,17,18,19,20-pentanor-5-prostenoic Acid Isopropyl Ester The above-mentioned prostaglandins are disclosed in U.S. Pat. No. 5,004,752 (Raduechel et al.) and EP 299 914 (Buchmann et al.). To the extent that U.S. Pat. No. 5,004,752 and EP 299 914 teach the preparation of the prostaglandins of the present invention, these patents are hereby incorporated by reference herein. The syntheses of some of the above-mentioned prostaglandins are detailed below in Examples 1 (Compound II), 2 (Compound III) and 3 (Compound IV).

In the examples below, the following standard abbreviations are used: g=grams (mg=milligrams); mol=moles (mmol=millimoles); mL=milliliters; mm Hg=millimeters of mercury; mp=melting point; bp=boiling point; h=hours; and min=minutes. In addition, "NMR" refers to nuclear magnetic resonance spectroscopy and "CI MS" refers to chemical ionization mass spectrometry.

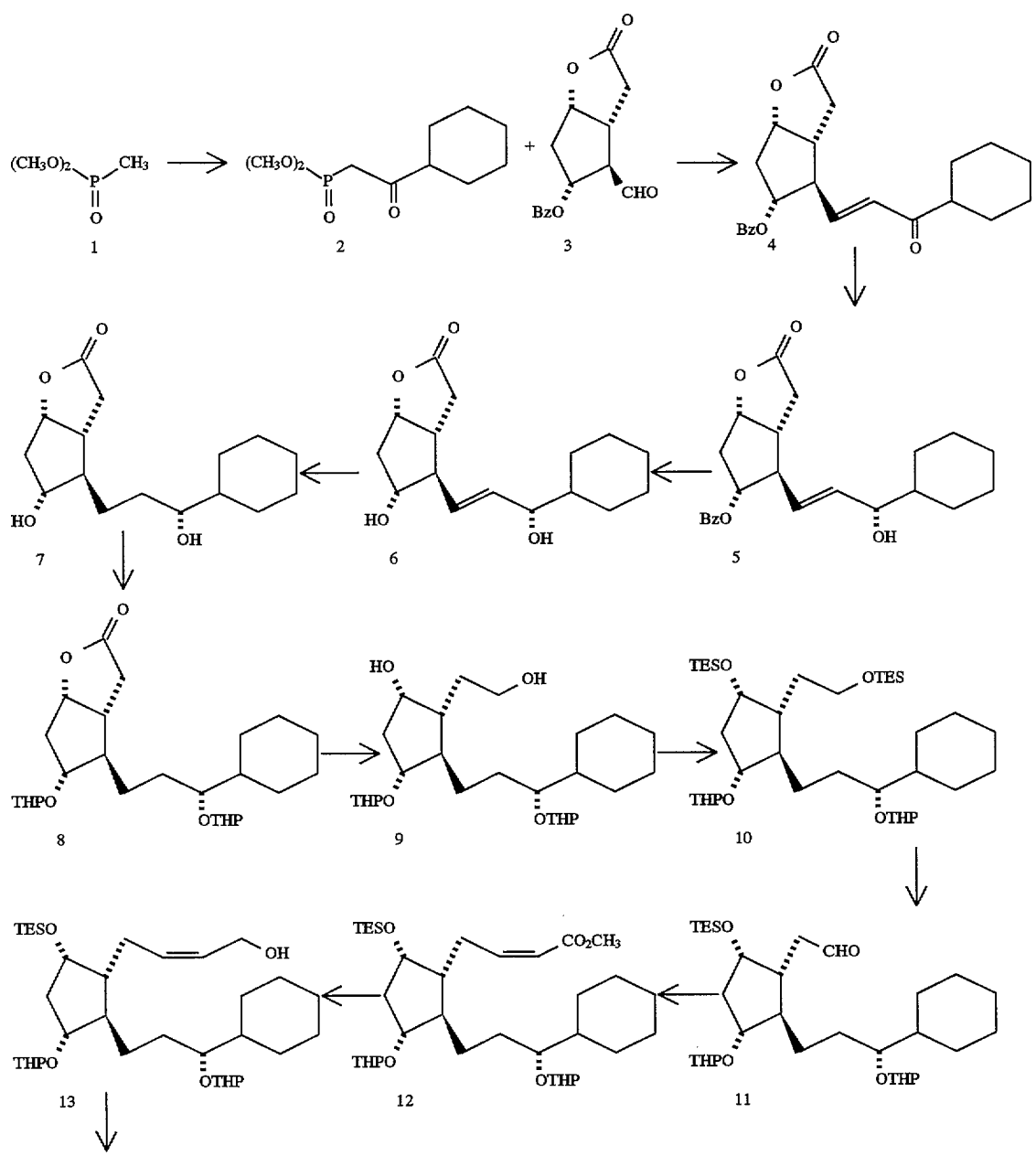

SCHEME I:
SYNTHESIS OF COMPOUND (II)

-continued
SCHEME I:
SYNTHESIS OF COMPOUND (II)

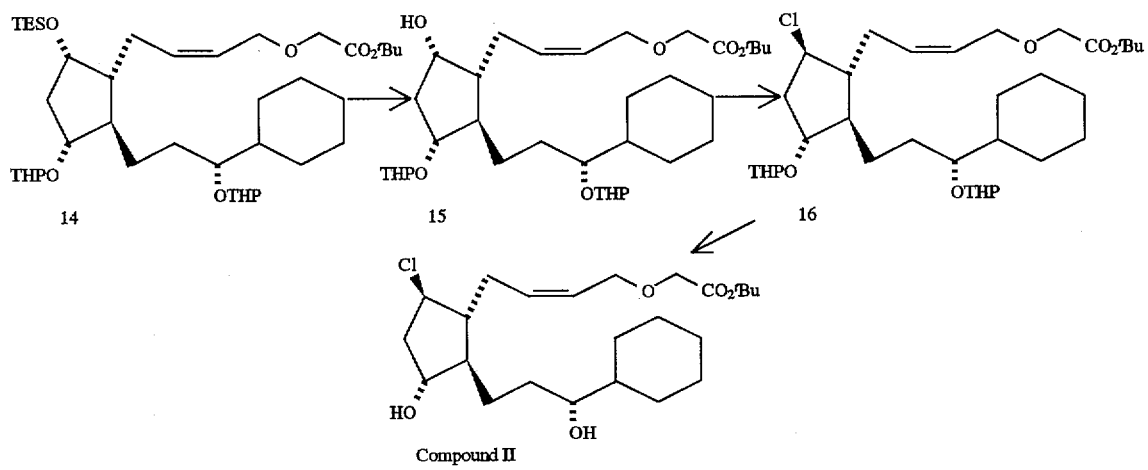

EXAMPLE 1

Synthesis of Compound (II)

A: Dimethyl (2-cyclohexyl-2-oxo)ethylphosphonate (2):

A solution of dimethyl methylphosphonate (100 g, 0.8 mol) in 1.0 L of anhydrous THF was cooled to −70° C. and n-BuLi (2.5M in hexanes, 320 mL, 0.8 mol) was added dropwise such that the temperature remained below −60° C. The mixture was stirred for 10 min at −70° C. and then methyl cyclohexanecarboxylate (57.3 mL, 0.4 mol) was added dropwise, via syringe, over a period of 15 min. The resulting mixture was then stirred for 14 h at room temperature. The reaction was quenched by first cooling to 0° C. followed by the addition of 2M HCl until the aqueous layer was at pH 2. The layers were separated and the aqueous layer was extracted with 2×200 mL of $CH_2Cl_2$. The organic layers were combined and washed sequentially with 200 mL each of water and brine and then dried ($MgSO_4$). Filtration and solvent removal gave a yellow oil which was distilled under vacuum to afford 67.3 g (72%) of 2 as a clear colorless liquid: bp 100°–115° C. (0.01 mmHg); $^1$H NMR ($CDCl_3$) δ 3.74 (d, J=12.0 Hz, 6H), 3.08 (d, J=22 Hz, 2H), 2.55 (m, 1H), 1.95-1.60 (m, 5H), 1.40-1.15 (m, 5H).

B: (3aR, 4R, 5R, 6aS)-5-(Benzoyloxy)-4-[(E)-3-cyclohexyl-3-oxo-1-propenyl]-hexahydro-2H-cyclopenta[b]furan-2-one (4):

A solution of anhydrous THF (1.4 L), LiCl (11.7 g, 0.28 mol) and the phosphonate 2 (67.0 g, 0.28 mol) was cooled to 0° C. and triethylamine (39.2 mL, 0.28 mol) was added dropwise. A solution of the aldehyde 3 (68.5 g, 0.25 mol) in dry $CH_2Cl_2$ (320 mL) was added dropwise to the cold suspension and the resulting mixture was stirred at 0° C. for 3 h. The reaction mixture was then poured into 500 mL of 2M HCl, and layers were separated. The aqueous layer was extracted with 500 mL of $CH_2Cl_2$. Combined organic layers were washed with 100 mL each of water and brine followed by drying over $MgSO_4$. Filtration and solvent removal gave a yellow solid which was recrystallized from EtOAc to afford 85.8 g (89%) of 4 as a white solid: mp 151°–153° C.; $^1$H NMR ($CDCl_3$) δ 8.01 (d, J=2.0 Hz, 2H), 7.65 -7.40 (m, 3H), 6.70 (dd, J=12, 6 Hz, 1H), 6.35 (d, J=12 Hz, 1H), 5.32 (m, 1H), 5.15 (m, 1H), 2.93 (m, 3H), 2.72-2.25 (m, 4H), 1.85-1.56 (m, 6H), 1.40-1.15 (m, 5H).

C: (3aR, 4R, 5R, 6aS)-5-(Benzoyloxy)-4-[(E)-(3S)-3-cyclohexyl-3-hydroxy-1-propenyl]-hexahydro-2H-cyclopenta[b]furan-2-one (5):

A solution of $CeCl_3.7H_2O$ (19.5 g, 52.3 mmol) and enone 4 (20.0 g, 52.3 mmol) in 150 mL of $CH_3OH$ and 70 mL of $CH_2Cl_2$ was prepared. $NaBH_4$ (1.92 g, 52.3 mmol) was added in small portions over a period of 5 min. The resulting mixture was stirred at ambient temperature for 45 min and then was poured into a separatory funnel containing 100 mL each of 25% (v/v) aqueous acetic acid and $CH_2Cl_2$. Layers were separated and the aqueous layer was extracted with 3×50 mL of $CH_2Cl_2$. Combined organic layers were washed with sat. $NaHCO_3$ (50 mL), and brine (50 mL), and then dried ($MgSO_4$). Upon solvent removal, 23.7 g of a colorless oil containing nearly equal amounts of the two diastereomeric allyl alcohols was obtained. Diastereomers were separated by HPLC (40% EtOAc/hexane), affording 5 (9.34 g (46%), the less polar component) as a white solid. $^1$H NMR ($CDCl_3$) δ 8.01 (d, J=8 Hz, 2H), 7.62-7.28 (m, 3H), 5.61 (m, 2H), 5.25 (m, 1H), 5.08 (m, 1H), 3.85 (m, 1H), 2.95-2.45 (m, 5H), 2.30 (m, 2H), 1.95-1.55 (m, 6H), 1.50-0.80 (m, 5H).

D: (3aR, 4R, 5R, 6aS)-4-[(3R)-3-Cyclohexyl-3-hydroxypropyl]-hexahydro-5-hydroxy-2H-cyclopenta[b]furan-2-one (7):

A solution of the allyl alcohol 5 (10.0 g, 26.0 mmol) in warm methanol (100 mL) was cooled to ambient temperature. Anhydrous $K_2CO_3$ (3.6 g, 26.0 mmol) was added and the resulting mixture was stirred at ambient temperature for 3 h. The reaction mixture was concentrated and the residue was partitioned between 100 mL each of EtOAc and 1M HCl. Layers were separated and the aqueous phase was extracted with 3×50 mL of EtOAc. Combined organic layers were washed with 50 mL of water, 2×50 mL of sat. $NaHCO_3$, 50 mL of brine, and dried over $MgSO_4$. Filtration and evaporation gave the diol 6 (9.8 g, 92% yield, $R_f$ 0.26, 100% EtOAc), which was used in the subsequent reaction without further purification.

The crude diol 6 (9.8 g, 26 mmol) was dissolved in 50 mL of EtOAc and a catalytic amount (0.1 g) of 5% Pd/C was added. This mixture was hydrogenated at 30–40 psi in a Parr hydrogenation apparatus for 3 h and then filtered through a short pad of Celite. The filtrate was concentrated and the crude yellow oil was purified by passage through a short column of silica ($R_f$ 0.26, EtOAc) to afford 7 (5.06 g, 70% yield from 5) as a colorless, viscous oil which solidified upon standing. $^1$H NMR ($CDCl_3$) δ 4.95 (m, 1H), 4.05 (m, 1H), 3.35 (m, 1H), 2.80 (m, 1H), 2.58 (m, 2H), 2.30 (m, 1H), 2.00 (m, 14H).

E: (3aR, 4R, 5R, 6aS)-4-[(3R)-3-Cyclohexyl-3-(tetrahydropyran-2-yloxy)propyl]-hexahydro-5-(tetrahydropyran-2-yloxy)-2H-cyclopenta[b]furan-2-one (8):

A solution of the diol 7 (6.0 g, 21.2 mmol) and dihydropyran (7.80 mL, 84.8 mmol) in $CH_2Cl_2$ (100 mL) was cooled to 0° C. A catalytic amount of p-TsOH (0.05 g, 0.26 mmol) was added and the mixture was stirred for 30 min at 0° C. The reaction was then quenched by adding sat. aqueous $NaHCO_3$ (10 mL). Layers were separated and the aqueous phase was extracted with 2×25 mL of $CH_2Cl_2$. Combined organic layers were dried over anhydrous $K_2CO_3$, filtered and concentrated to afford a colorless oil which was purified by passage through a short column of silica ($R_f$ 0.46, 1:1 EtOAc/hexanes). The bis-THP ether 8 (8.59 g, 89% yield) was isolated as a colorless oil which solidified upon standing. $^1H$ NMR ($CDCl_3$) δ (characteristic peaks only) 5.00 (m, 1H), 4.75-4.45 (m, 2H), 3.85 (m, 2H), 3.60-3.30 (m, 4H).

F: (9S, 11R, 15R)-11,15-Bis-(tetrahydropyran-2-yloxy)-15-cyclohexyl-2,3,4,5,6,16,17,18,19,20-decanor-9-(triethylsilyloxy)prostanol Triethylsilyl Ether (10):

A suspension of lithium aluminum hydride (1.43 g, 38.0 mmol) in 50 mL of anhydrous THF was cooled to 0° C. and a solution of the lactone 8 (8.59 g, 19.0 mmol) in THF (100 mL) was added dropwise. The resulting mixture was stirred at 0° C. for 3 h after which 1.5 mL of $H_2O$, 1.5 mL 15% NaOH and 4.5 mL of $H_2O$ were sequentially added. After warming to ambient temperature, 100 mL of EtOAc was added and solids were filtered off. The filter cake was washed thoroughly with 3×50 mL of EtOAc and the filtrates were dried by passage through a short pad anhydrous $MgSO_4$. Evaporation afforded 9 (9.02 g) as a colorless oil which was used in the subsequent step without further purification ($R_f$ 0.31, 80:20 EtOAc/hexanes).

A mixture of the crude diol 9 (9.02 g, 19.0 mmol), triethylsilyl chloride (9.65 mL, 57.0 mmol), dimethylaminopyridine (0.41 g, 3.42 mmol), triethylamine (16.0 mL, 114 mmol) and anhydrous N,N-dimethylformamide (50 mL) was stirred at ambient temperature for 14 h under $N_2$. The reaction mixture was then diluted with 250 mL of $CH_2Cl_2$ and the solution was washed with 3×50 mL $H_2O$. Combined water washes were extracted with 2×50 mL of $CH_2Cl_2$. Organic layers were combined, dried ($MgSO_4$), filtered and concentrated to afford a yellow oil which was chromatographed on silica ($R_f$ 0.4, 1:9 EtOAc/hexanes). Pure 10 (11.23 g, 86% yield from 8) was obtained as a slightly yellow oil. $^1H$ NMR ($CDCl_3$) δ (characteristic peaks only) 4.62 (m, 2H), 4.15-3.25 (broad m, 7H), 2.30-1.15 (broad m, 18H), 0.95 (broad t, 18H), 0.65 (broad q, 12H).

G: (9S, 11R, 15R)-11,15-Bis-(tetrahydropyran-2-yloxy)-15-cyclohexyl-2,3,4,5,6,16,17,18,19,20-decanor-9-(triethylsilyloxy)prostanal (11):

A solution of oxalyl chloride (0.51 mL, 0.57 mmol) in anhydrous $CH_2Cl_2$ (15 mL) was cooled to −78° C. under $N_2$. A solution of anhydrous DMSO (0.81 mL, 11.4 mmol) in $CH_2Cl_2$ (2.0 mL) was then added dropwise. After 2 min, a solution of 10 (2.6 g, 3.8 mmol) in 8 mL of dry $CH_2Cl_2$ was introduced dropwise via syringe over a period of 2 min. The resulting mixture was stirred at −78° C. for 2 h at which time triethylamine (2.7 mL, 19.0 mmol) was added. The reaction was stirred for 15 min and then allowed to warm to ambient temperature. The mixture was partitioned between 100 mL of EtOAc and 10 mL of $H_2O$ and the organic layer was washed with an additional 10 mL $H_2O$, 10 mL of brine and dried ($MgSO_4$). Solvent removal gave a yellow oil which was subjected to chromatography on silica gel ($R_f$ 0.2, 10% EtOAc/hexanes) to afford 11 (1.4 g, 65% yield) and some starting material (0.83 g). $^1H$ NMR ($CDCl_3$) δ 9.80 (broad s, 1H), 4.62 (m, 2H), 4.20 (m, 1H), 3.85-3.60 (m, 3H), 3.40 (m, 3H), 2.80 (m, 1H), 2.45-2.05 (m, 4H), 1.95-1.10 (broad m, 27H), 0.95 (broad t, 9H), 0.55 (broad q, 6H).

H: (5Z)-(9S, 11R, 15R)-11,15-Bis-(tetrahydropyran-2-yloxy)-15-cyclohexyl-2,3,4,16,17,18,19,20-octanor-9-(triethylsilyloxy)-5-prostenoic Acid Methyl Ester (12):

A solution of 18-crown-6 (8.50 g, 32.1 mmol) and bis(2,2,2-trifluoroethyl) (methoxycarbonylmethyl)phosphonate (3.72 g, 11.7 mmol) in 110 mL of THF was cooled to −78° C. KHMDS (0.5M in toluene, 23.4 mL, 11.7 mmol) was added to the above mixture and the solution was stirred for 15 min. Aldehyde 11 (6.11 g, 10.7 mmol) in 5.0 mL of THF was added dropwise over a period of 15 min. The reaction was stirred at −78° C. for 2 h, then warmed up to 0° C. and stirred at that temperature for 2 more hours. The reaction was quenched by adding 50 mL of saturated aqueous $NH_4Cl$ and the mixture was allowed to warm to room temperature. Layers were separated and the aqueous layer was extracted with 2×50 mL of EtOAc. Combined organic layers were washed with 2×50 mL of brine and dried ($K_2CO_3$). Filtration and solvent removal gave a crude yellow oil which was purified by passage through a short plug of silica to afford a mixture of 12 and its E isomer (9:1 ratio, 6.28 g, 95% yield). Isomers were separated by chromatography on silica gel ($R_f$ 0.56, and 0.47, for the major and minor isomers respectively, 40% $Et_2O$/hexane); 4.57 g of pure 12 and 0.97 g of a 1:1 E/Z mixture were isolated. $^1H$ NMR ($CDCl_3$) δ 6.35 (m, 1H), 5.78 (broad d, J=12.0 Hz, 1H), 4.65 (m, 2H), 4.28 (m, 1H), 3.90 (m, 2H), 3.70 (s, 3H), 3.55-3.30 (m, 3H), 2.80 (m, 2H), 2.35-2.05 (m, 1H), 2.00-1.10 (broad m, 30H), 0.95 (broad t, 9H), 0.60 (broad q, 6H).

I: (5Z)-(9S, 11R, 15R)-11,15-Bis-(tetrahydropyran-2-yloxy)-15-cyclohexyl-2,3,4,16,17,18,19,20-octanor-9-(triethylsilyloxy)-5-prosten-1-ol (13):

A solution of 12 (2.0 g, 3.22 mmol) in 20 mL of anhydrous THF was cooled to 0° C. under $N_2$. A solution of diisobutylaluminum hydride (1.5M in toluene, 6.5 mL, 9.66 mmol) was added dropwise and the resulting mixture was stirred at 0° C. for 2 h. The reaction was then quenched by careful addition of $CH_3OH$ (5 mL), allowed to warm up to ambient temperature, and diluted with 50 mL of THF. The resulting cloudy solution was treated with 50 mL of a saturated aqueous solution of sodium potassium tartrate and the biphasic mixture was stirred for 1 h. Layers were then separated and the aqueous layer was extracted with 2×50 mL of THF. Organic extracts were combined, washed with brine (50 mL), and dried ($MgSO_4$). Filtration and solvent removal gave a pale yellow oil which was purified by chromatography on silica gel ($R_f$ 0.26, 4:6 $Et_2O$/hexane) to yield 13 (1.95 g, 95% yield) as a colorless oil. This compound was used immediately in the subsequent reaction. $^1H$ NMR ($CDCl_3$) δ 5.65 (m, 2H), 4.65 (m, 2H), 4.30-3.25 (broad m, 5H), 2.40-2.05 (broad m, 4H), 2.00-1.10 (broad m, 32H), 1.00 (broad t, 9H), 0.60 (broad q, 6H).

J: (5Z)-(9S, 11R, 15R)-11,15-Bis-(tetrahydropyran-2-yloxy)-15-cyclohexyl-9-hydroxy-3-oxa-16,17,18,19,20-pentanor-5-prostenoic Acid t-Butyl Ester (15):

A mixture of 13 (1.95 g, 3.28 mmol), t-butyl bromoacetate (5.11 g, 26.24 mmol), tetrabutylammonium hydrogen sulfate (0.8 g, 2.35 mmol), toluene (45 mL) and 25% (wt/wt) aqueous NaOH (30 mL) was stirred vigorously at room temperature for 18 h. Layers were separated and the aqueous layer was extracted with 2×25 mL of EtOAc. Combined organic extracts were washed with brine (15 mL), dried ($MgSO_4$), and concentrated. Crude product was purified by chromatography on silica gel ($R_f$ 0.56, 20% EtOAc/hexane) to yield 2.19 g of 14 (contaminated with some t-butyl bromoacetate) and 0.48 g of the starting allyl alcohol 13. The allyl ether 14 thus obtained was used in the desilylation reaction without further purification.

The silyl ether 14 (0.5 g) obtained above was dissolved in 3.0 mL of DMSO and to it was added 2.2 mL of tetrabutylammonium fluoride (1.0M in THF, 2.2 mmol). The mixture was stirred at ambient temperature for 30 min and then partitioned between 50 mL EtOAc and 10 mL brine. The aqueous layer was extracted with 2×10 mL of EtOAc and the combined organic extracts were dried over $MgSO_4$. Evaporation and chromatography on silica gel ($R_f$ 0.44, 50% EtOAc/hexane) afforded 0.28 g of 15 as a colorless oil. $^1H$ NMR ($CDCl_3$) δ 5.65 (m, 2H), 4.62 (m, 2H), 4.16 (m, 1H), 4.10-3.75 (m, 3H), 3.95 (s, 2H), 3.45 (m, 2H), 2.50-0.90

The hydroxyester 15 (0.28 g, 0.47 mmol) was dissolved in 4.0 mL of a stock solution containing 48.0 mL of $CH_3CN$, 0.79 mL of pyridine, and 0.97 mL of $CCl_4$. Triphenylphosphine (0.18 g, 0.70 mmol) was added and the resulting mixture was stirred at ambient temperature for 17 h. The reaction mixture was treated with 10 mL of a 1:1 solution of $Et_2O$/hexanes and the precipitate formed was filtered off. The filtrate was concentrated and purified by chromatography (silica gel, $R_f$ 0.47, 40:60 $Et_2O$/hexanes) to yield pure 16 (90 mg, 34%) as a colorless oil.

A solution of 16 (80 mg, 0.13 mmol) in 7.0 mL of 65% (v/v) aqueous acetic acid was heated to 65°–70° C. for 45 min. The reaction mixture was cooled to room temperature and concentrated. The resulting residue was redissolved in anhydrous EtOH and the solvent was again evaporated. The residue thus obtained was purified by chromatography on silica gel ($R_f$ 0.4, 60:40 EtOAc/hexanes) to yield 60 mg (100%) of Compound (II) as a colorless, viscous oil. $^1H$ NMR ($CDCl_3$) δ 5.69 (m, 2H), 4.32-3.85 (m, 5H), 3.38 (m, 1H), 2.50-1.95 (m, 5H), 1.95-0.80 (broad m, 29H) 1.43 (s, 9H); $^{13}C$ NMR ($CDCl_3$) δ 169.9, 131.7, 126.8, 82.0, 75.6, 75.1, 67.9, 66.6, 54.2, 51.0, 44.3, 43.7, 31.4, 30.3, 30.1, 29.3, 28.1, 28.0, 26.5, 26.3, 26.1; High Resolution CI MS m/z calcd for $C_{24}H_{42}O_5Cl$ ($MH^+$) 445.2720, found 445.2716.

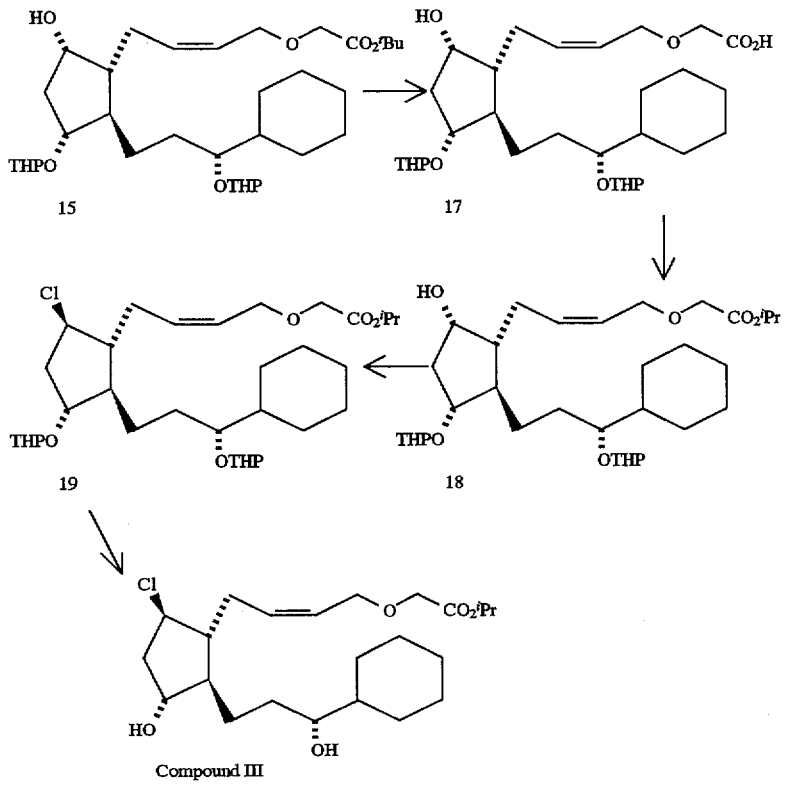

SCHEME II:
SYNTHESIS OF COMPOUND (III)

(broad m, 35H), 1.46 (s, 9H); High Resolution CI MS m/z (CI) calcd for $C_{34}H_{59}O_8$ ($MH^+$) 595.4209, found 595.4208.

K: (5Z)-(9R, 11R, 15R)-9-Chloro-15-cyclohexyl-11,15-dihydroxy-3-oxa-16,17,18,19,20-pentanor-5-prostenoic Acid t-Butyl Ester (Compound (II)):

EXAMPLE 2

Synthesis of Compound (III)

A: (5Z)-(9S, 11R, 15R)-11,15-Bis-(tetrahydropyran-2-yloxy)-15-cyclohexyl-9-hydroxy-3-oxa-16,17,18,19,20-pentanor-5-prostenoic Acid (17):

Hydroxyester 15 (0.454 g; 0.76 mmol; see Example 1) was dissolved in 10 mL of methanol and 2 mL of water. Lithium hydroxide monohydrate (0.16 g; 500 mol %) was added and the mixture was stirred at room temperature. After 18 h, 20 mL of saturated, aqueous $KH_2PO_4$ and 20 mL $CH_2Cl_2$ were added, layers were separated, and the aqueous phase was washed with additional $CH_2Cl_2$ (3×20 mL). Combined organic layers were dried over $Na_2SO_4$, filtered, and concentrated, affording 0.47 g of a colorless oil which was used directly in the next reaction.

B: (5Z)-(9S, 11R, 15R)-11,15-Bis-(tetrahydropyran-2-yloxy)-15-cyclohexyl-9-hydroxy-3-oxa-16,17,18,19,20-pentanor-5-prostenoic Acid Isopropyl Ester (18):

Crude acid 17 from above (0.23 g; 0.43 mmol) was dissolved in 10 mL of acetone. DBU (0.25 mL; 400 mol %) and isopropyl iodide (0.21 g; 300 mol %) were added and the mixture was then cooled to room temperature and concentrated. The resulting residue was then purified by silica gel chromatography (hexane/EtOAc, 2/3), affording 27 mg (25% based on 18) of pure Compound (III) ($R_f$=0.56) as a colorless oil with 69 mg of a mixture of Compound (III) and its 5,8-diene elimination product ($R_f$=0.45). $^1$H NMR ($CDCl_3$) δ 5.67 (m, 2H), 5.08 (sep, 1H, J=6.1), 4.30-3.95 (m, 6H), 3.40 (m, 1H), 2.35 (m, 2H), 2.30-2.00 (m, 3H), 1.93-1.35 (m, 12H), 1.25 (d, 6H, J=6.2 Hz), 1.22-0.90 (m, 6H); $^{13}$C NMR ($CDCl_3$) δ 170.2, 131.8, 126.7, 75.7, 75.2, 68.8, 67.6, 66.7, 61.2, 54.2, 51.1, 44.4, 43.6, 31.4, 30.2, 30.1, 29.3, 28.0, 26.5, 26.3, 26.1, 21.8; High Resolution CI MS m/z calcd for $C_{23}H_{40}O_5Cl$ ($MH^+$) 431.2564, found 431.2569.

SCHEME III:
SYNTHESIS OF COMPOUND (IV)

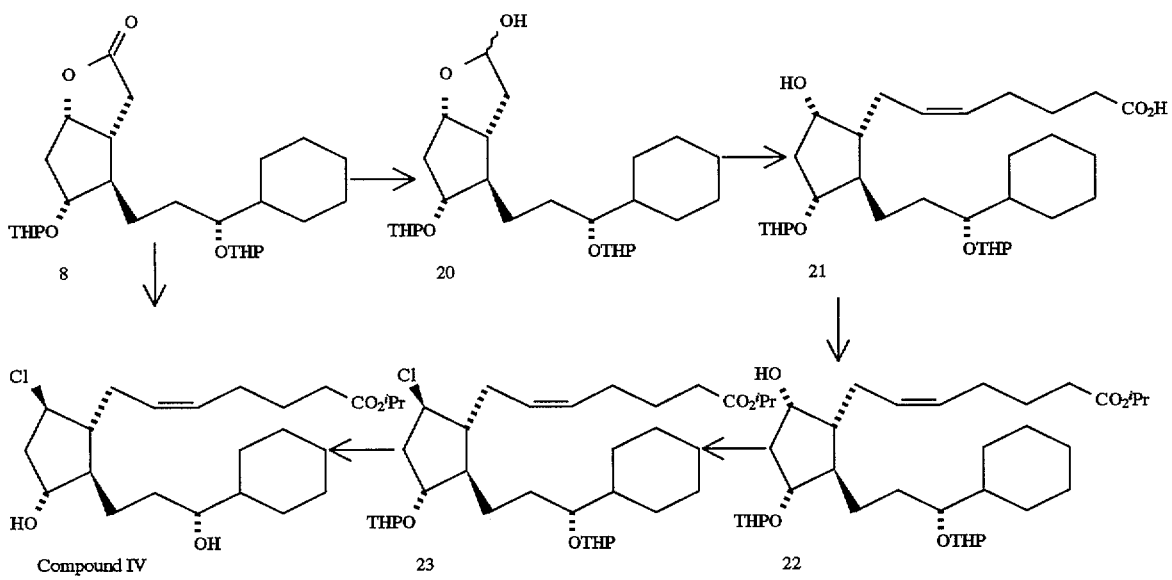

mixture was stirred for 12 h at room temperature. After evaporation, the residue was applied to a silica gel column and eluted with hexane/EtOAc, 1/1, to afford 0.157 g (63%) of isopropyl ester 18 as a colorless oil. $R_f$=0.49; $^1$H NMR ($CDCl_3$) δ (characteristic peaks only) 5.80-5.52 (m, 2H), 5.15 (sep, 1H, J=6.2 Hz), 4.03 (broad s, 2H), 1.27 (d, 6H, J=6.2 Hz).

C: (5Z)-(9R, 11R, 15R)-9-Chloro-15-cyclohexyl-11,15-dihydroxy-3-oxa-16,17,18,19,20-pentanor-5-prostenoic Acid Isopropyl Ester (Compound III):

The hydroxyester 18 (0.146 g; 0.25 mmol) was dissolved in 3.0 mL of a stock solution containing 48 mL of $CH_3CN$, 0.79 mL of pyridine, and 0.97 mL of $CCl_4$. Triphenylphosphine (0.10 g; 150 mol %) was added and the resulting mixture was stirred at room temperature for 17 h. The reaction mixture was treated with 10 mL of a 1:1 solution of $Et_2O$/hexanes and the precipitate was filtered off. The filtrate was concentrated and chromatographed on silica gel (hexane/EtOAc, 4/1), affording 0.108 g of a colorless oil which consisted of a nearly equimolar mixture of desired chlorinated material 19 with its undesired 5,8-diene elimination product.

A solution of crude 19 from above in 10 mL of 65% (v/v) aqueous acetic acid was warmed to 65° C. for 45 min. The

EXAMPLE 3

Synthesis of Compound (IV)

A: (5Z)-(9S, 11R, 15R)-11,15-Bis-(tetrahydropyran-2-yloxy)-15-cyclohexyl-9-hydroxy-16,17,18,19,20-pentanor-5-prostenoic Acid Isopropyl Ester (22):

To a solution of 5.0 g (11 mmol) of lactone 8 (see Example 1) in 40 mL of THF at −78° C. was added dropwise 9.6 mL (14.4 mmol) of a 1.5M solution of diisobutylaluminum hydride in toluene. After 1.5 h, 5 mL of MeOH was added, the mixture was stirred for 10 min at −78° C. and then warmed to room temperature. This solution was then added to a mixture of 20 mL of saturated, aqueous $NH_4Cl$, 35 mL of EtOAc, and 35 mL of saturated, aqueous sodium potassium tartrate. The mixture was stirred for 20 min, layers were separated, and the aqueous layer was washed with EtOAc (3×40 mL). Combined organic layers were dried over $MgSO_4$, filtered, and evaporated. The resulting residue was purified by silica gel chromatography (EtOAc/hexane, 1/1), affording 4.5 g (90%) of lactol 20 which was used directly in the next reaction.

To a solution of 14.1 g (31.8 mmol) of (1-carboxypent-5-yl)triphenylphosphonium bromide in 100 mL of THF at 0°

C. was added dropwise 59 mL (59 mmol) of a 1M solution of potassium t-butoxide in THF. After 20 min, 4.5 g (9.9 mmol) of lactol 17 in 20 mL of THF was added dropwise. The reaction was quenched after 2 h by pouring into 150 mL of a 1/1 (v/v) mixture of EtOAc/saturated, aqueous $NH_4Cl$. Layers were separated and the aqueous layer was extracted with EtOAc (3×70 mL). Combined organic layers were dried over $MgSO_4$, filtered and evaporated, leaving 7.6 g of crude acid 21 as an oil.

Crude acid 21 (7.6 g) was dissolved in 55 mL of acetone, cooled to 0° C., and 8.6 g (56 mmol) of DBU was added dropwise. The reaction was warmed to room temperature and 8.5 g (50 mmol) of isopropyl iodide was added dropwise. After stirring for 14 h, the mixture was poured into 100 mL of a 1/1 (v/v) mixture of EtOAc/saturated, aqueous $NH_4Cl$. Layers were separated and the aqueous phase was extracted with additional EtOAc (2×100 mL). Combined organic layers were dried over $MgSO_4$, filtered, evaporated, and chromatographed on silica gel (EtOAc/hexane, 2/3) affording 1.98 g (35% from lactol 20) of 22. $^1$H NMR ($CDCl_3$) δ (characteristic peaks only) 5.58-5.28 (m, 2H), 4.97 (sep, J=6.2 Hz, 1H), 1.1 (d, J=6.2 Hz, 6H).

B: (5Z)-(9R, 11R, 15R)-9-Chloro-15-cyclohexyl-11,15-dihydroxy-16,17,18,19,20-pentanor-5-prostenoic Acid Isopropyl Ester (Compound IV):

Hydroxyester 22 (513.1 mg; 0.8864 mmol) was dissolved in 6.6 mL of a stock solution containing 48.0 mL of $CH_3CN$, 0.79 mL of pyridine, and 0.97 mL of $CCl_4$. Triphenylphosphine (348.8 mg; 150 mol %) was added and the mixture was stirred for 45 h at room temperature. The reaction was then diluted with 7 mL of $Et_2O$ and 14 mL of hexane. After stirring for 10 min, solids were filtered off and the filtrate was evaporated. The resulting solids were triturated three times with 15 mL of hexane/$Et_2O$ (1/2). Combined hexane/$Et_2O$ washes were concentrated down to 0.75 g of a white solid which was then redissolved in hexane/$Et_2O$ and chromatographed on silica gel. Elution with hexane/$Et_2O$, 5/1, afforded 372.8 mg of semipure 23 which was used directly in the next reaction.

Crude 23 from above was dissolved in 20 mL of 65% (v/v) aqueous HOAc and warmed to room temperature. After 1.5 h, the reaction was concentrated, 15 mL of $H_2O$ was added, and the solution was reconcentrated. Absolute EtOH (15 mL) was added followed, again, by reconcentration. The resulting oil was purified by silica gel chromatography (hexane/EtOAc, 2/1), affording 244.1 mg of a mixture of Compound (IV) contaminated with an approximately equal quantity of the 5,8-diene side product. An 8.2 mg sample was then further purified by reverse phase HPLC, giving 4.4 mg of pure Compound (IV) as a clear, viscous oil. $^1$H NMR ($CDCl_3$) δ 5.47 (m, J=8.5 Hz, 2H), 5.01 (sep, J=6.3 Hz, 1H), 4.10 (dt, J=4.0, 6.2 Hz, 1H), 4.04 (q, J=7.6 Hz, 1H), 3.37 (m, 1H), 2.35-2.24 (m, 4H), 2.20-2.07 (m, 4 H), 1.82 (br s, 2H), 1.80-1.50 (m, 13H), 1.36-0.96 (m, 12H). $^{13}$C NMR ($CDCl_3$) δ 173.2, 131.0, 126.8, 76.2, 76.0, 67.5, 60.8, 54.3, 51.7, 44.5, 43.5, 34.0, 31.7, 30.0, 29.2 (two overlapping resonances), 27.9, 26.6, 26.4, 26.2, 26.1, 24.9, 21.8. High Resolution CI MS m/z calcd for $C_{24}H_{42}O_4Cl$ ($MH^+$) 429.2772, found 429.2763.

The compounds of formula (I) are useful in lowering intraocular pressure and thus are useful in the treatment of glaucoma. The preferred route of administration is topical. The dosage range for topical administration is generally between about 0.001 and about 1000 micrograms per eye (μg/eye) and is preferably between about 0.01 and about 100 μg/eye and most preferably between about 0.05 and about 50 μg/eye. The compounds of the present invention can be administered as solutions, suspensions, or emulsions (dispersions) in a suitable ophthalmic vehicle.

In forming compositions for topical administration, the compounds of the present invention are generally formulated as between about 0.0001 to about 0.5 percent by weight (wt %) solutions in water at a pH between about 4.5 and about 8.0. It is preferable to use concentrations between about 0.0005 to about 0.1 wt % and, most preferably, between about 0.001 and about 0.1 wt %. While the precise regimen is left to the discretion of the clinician, it is recommended that the resulting solution be topically applied by placing one drop in each eye one or two times a day.

Other ingredients which may be desirable to use in the ophthalmic preparations of the present invention include preservatives, co-solvents and viscosity building agents.

Antimicrobial Preservatives:

Ophthalmic products are typically packaged in multidose form, which generally require the addition of preservatives to prevent microbial contamination during use. Suitable preservatives include: benzalkonium chloride, thimerosal, chlorobutanol, methyl paraben, propyl paraben, phenylethyl alcohol, edetate disodium, sorbic acid, ONAMER M®, or other agents known to those skilled in the art. Such preservatives are typically employed at a concentration between about 0.001 and about 1.0 wt %.

Co-Solvents:

Prostaglandins, and particularly ester derivatives, typically have limited solubility in water and therefore may require a surfactant or other appropriate co-solvent in the composition. Such co-solvents include: Polysorbate 20, 60 and 80; Pluronic F-68, F-84 and P-103; Tyloxapol; Cremophor EL, sodium dodecyl sulfate; glycerol; PEG 400; propylene glycol; cyclodextrins; or other agents known to those skilled in the art. Such co-solvents are typically employed at a concentration between about 0.01 and about 2 wt %.

Viscosity Agents:

Viscosity greater than that of simple aqueous solutions may be desirable to increase ocular absorption of the active compound, to decrease variability in dispensing the formulations, to decrease physical separation of components of a suspension or emulsion of formulation and/or otherwise to improve the ophthalmic formulation. Such viscosity building agents include: polyvinyl alcohol; polyvinyl pyrolidone; cellulosic polymers, such as methyl cellulose, hydroxy propyl methylcellulose, hydroxyethyl cellulose, carboxymethyl cellulose, hydroxy propyl cellulose; carboxy vinyl polymers, such as carbomer 910, carbomer 940, carbomer 934P and carbomer 1342; or other agents known to those skilled in the art. Such agents are typically used at a concentration between about 0.01 and about 2 wt %.

EXAMPLE 4

The following Formulations A–D are representative pharmaceutical compositions of the invention for topical use in lowering of intraocular pressure. Each of Formulations A–D may be formulated in accordance with procedures known to those skilled in the art.

| Ingredient | Amount (wt %) |
| --- | --- |
| Formulation A: | |
| Compound (II) | 0.01 |
| Monobasic sodium phosphate | 0.05 |
| Dibasic sodium phosphate (anhydrous) | 0.15 |

-continued

| Ingredient | Amount (wt %) |
|---|---|
| Sodium chloride | 0.75 |
| Disodium EDTA (Edetate disodium) | 0.01 |
| Benzalkonium chloride | 0.02 |
| Polysorbate 80 | 0.5 |
| HCl and/or NaOH | pH 7.3–7.4 |
| Purified water | q.s. to 100% |
| Formulation B: | |
| Compound (III) | 0.01 |

-continued

| Ingredient | Amount (wt %) |
|---|---|
| Monobasic sodium phosphate | 0.05 |
| Dibasic sodium phosphate (anhydrous) | 0.15 |
| Sodium chloride | 0.75 |
| Disodium EDTA (Edetate disodium) | 0.05 |
| Cremophor EL | 0.1 |
| Benzalkonium chloride | 0.01 |
| HCl and/or NaOH | pH 7.3–7.4 |
| Purified water | q.s. to 100% |
| Formulation C: | |
| Formula (I), wherein: $R_1 = CO_2R_2$, $R_2 = H$, $X = \beta(R)Cl$, $Y = O$, $R_3 = R_4 = OH$, and $n = 1$ | 0.1 |
| Monobasic sodium phosphate | 0.05 |
| Dibasic sodium phosphate (anhydrous) | 0.15 |
| Sodium chloride | 0.5 |
| Hydroxypropyl-β-cyclodextrin | 4.0 |
| Benzalkonium chloride | 0.01 |
| NaOH and/or HCl | pH 6.3–6.6 |
| Purified water | q.s. to 100% |
| Formulation D: | |
| Formula (I), wherein: $R_1 = CO_2R_2$, $R_2 = H$, $X = \beta(R)Cl$, $Y = CH_2$, $R_3 = R_4 = OH$, and $n = 0$ | 0.2 |
| Monobasic sodium phosphate | 0.05 |
| Dibasic sodium phosphate (anhydrous) | 0.15 |
| Sodium chloride | 0.6 |
| Tyloxapol | 0.5 |
| Benzalkonium chloride | 0.02 |
| NaOH and/or HCl | pH 6.3–6.6 |
| Purified water | q.s. to 100% |

EXAMPLE 5

The ability of certain compounds of the present invention to reduce intraocular pressure (IOP) was evaluated in cynomolgus monkeys with ocular hypertension produced by previous laser trabeculoplasty in the right eye. Animals had been trained to sit in restraint chairs and conditioned to accept experimental procedures without chemical restraint. IOP was determined with a pneumatonometer after light corneal anesthesia with dilute proparacaine. The test protocol included a treatment regimen consisting of 5 divided doses administered over a period of 2 and ½ days. Doses 2–5 were given 8, 24, 32 and 48 hours after the initial dose. Baseline IOP values were determined prior to treatment with the test formulation, and then IOP was determined 16 hours after the fourth dose, and 2, 4 and 6 hours after the fifth dose. Prostaglandin doses are micrograms of compound contained in each treatment.

The two compounds tested are those previously identified as Compounds (II) and (IV).

TABLE 1

| Compound | PG Dose | Baseline IOP (mm Hg) | Percent IOP Reduction at Hours after Dose/Dose# | | | |
|---|---|---|---|---|---|---|
| | | | 16/4 | 2/5 | 4/5 | 6/5 |
| (II) | 5 µg | 36.3 | 38.3 ± 3.0 | 47.5 ± 5.1 | 43.7 ± 5.6 | 36.5 ± 5.8 |
| (II) | 1 µg | 36.9 | 22.3 ± 2.7 | 30.8 ± 4.7 | 26.4 ± 4.7 | 24.9 ± 4.0 |
| (IV) | 20 µg | 32.6 | 13.9 ± 2.7 | 30.1 ± 4.8 | 22.4 ± 5.2 | 19.3 ± 4.3 |

Results are presented in Table 1, above, and in FIG. 1. Compounds (II) and (IV) produced significant reduction of intraocular pressure at doses which are marginal or ineffective for other prostaglandins in published clinical studies. Compound (II) was especially potent, producing almost 50% reduction of intraocular pressure with just 5 µg of compound. In contrast, Nakajima et al. (*Graefe's Arch. Clin. Exp. Ophthalmol.*, 229:411–413 (1991)) reported that 50 µg of $PGD_2$ and 2.5 µg of BW245C (a $PGD_2$ analogue) reduce intraocular pressure in human eyes by 12% and 10%, respectively. Other studies (Woodward et al., *Invest. Ophthalmol. Vis. Sci.*, 31:138–146 (1990)) reported for these reference compounds in rabbits describe a maximum IOP reduction of approximately 28% for 250 µg of $PGD_2$ and 22% for 25 µg of BW245C. These comparisons indicate the unexpected potency of compounds of the present invention in reducing intraocular pressure. No indications of inflammation were observed during these studies.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A method of treating glaucoma and ocular hypertension which comprises topically administering to the affected eye a therapeutically effective amount of a compound of formula:

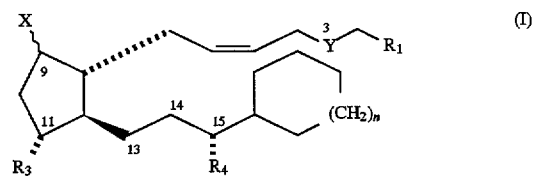

wherein:

$R_1 = CO_2R_2$, wherein $R_2 = H$, a cationic salt moiety, or an ophthalmically acceptable ammonium moiety; or $R_1$ may also represent an ophthalmically acceptable ester moiety;

X=halogen;

Y=$CH_2$ or O;

$R_3$, $R_4$ can be the same or different, and are selected from: free or functionally modified hydroxy groups; and n=0 or 1.

2. The method of claim 1, wherein: $R_1$ represents an ophthalmically acceptable ester moiety of the formula: $CO_2R_2$, wherein $R_2$=substituted or unsubstituted alkyl, cycloalkyl, (cycloalkyl)alkyl, aryl, or arylalkyl, and wherein substituents are selected from the group consisting of: alkyl, halogen, a free or functionally modified hydroxy group, or a free or functionally modified thiol; and X=F or Cl in either configuration.

3. The method of claim 2, wherein: $R_2$=H, methyl, ethyl, n-propyl, isopropyl, t-butyl or benzyl; X=Cl in the β (R) configuration; Y=O; $R_3$ and $R_4$=OH; and n=1.

4. The method of claim 3, wherein: $R_2$=isopropyl or t-butyl.

5. The method of claim 2, wherein: $R_2$=H, methyl, ethyl, n-propyl, isopropyl, t-butyl, or benzyl; X=Cl in the β (R) configuration; Y=$CH_2$; $R_3$ and $R_4$=OH; and n=1.

6. The method of claim 5, wherein: $R_2$=isopropyl.

7. The method of claim 1, wherein between about 0.001 and about 1000 micrograms of a compound of formula (I) is administered.

8. The method of claim 7, wherein between about 0.01 and about 100 micrograms of a compound of formula (I) is administered.

9. The method of claim 8, wherein between about 0.05 and about 50 micrograms of a compound of formula (I) is administered.

* * * * *

UNITED STATES PATENT AND TRADEMARK OFFICE
CERTIFICATE OF CORRECTION

PATENT NO. : 5,721,273
DATED : February 24, 1998
INVENTOR(S) : Verney L. Sallee, et al It is certified that error appears in the above-indentified patent and that said Letters Patent is hereby corrected as shown below:

Column 2: Between Lines 51 and 60, replace

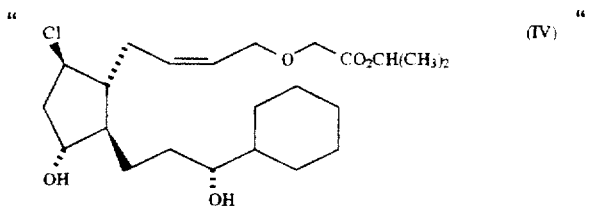

with

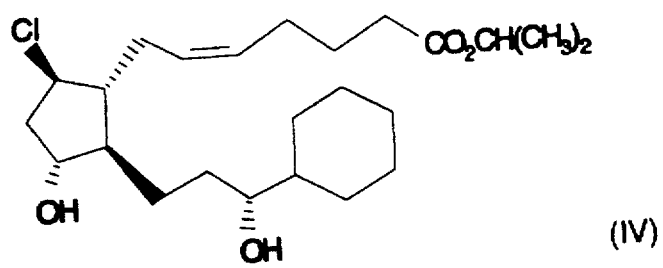

UNITED STATES PATENT AND TRADEMARK OFFICE
CERTIFICATE OF CORRECTION

PATENT NO. : 5,721,273
DATED : February 24, 1998
INVENTOR(S) : Verney L. sallee, et al It is certified that error appears in the above-indentified patent and that said Letters Patent is hereby corrected as shown below:

Column 11: Between Lines 16 and 44, under "SCHEME III: SYNTHESIS OF COMPOUND (IV)", delete the down arrow "↓" between the structures for compound "8" and Compound IV.

Signed and Sealed this

Twenty-first Day of July, 1998

Attest:

BRUCE LEHMAN

Attesting Officer

Commissioner of Patents and Trademarks